(12) United States Patent
Schopperle et al.

(10) Patent No.: US 10,509,038 B2
(45) Date of Patent: Dec. 17, 2019

(54) PODOCALYXIN AND TRA-RELATED ANTIBODY, METHODS OF PREPARATION AND USES AS AN ANTI-CANCER THERAPEUTIC AGENT

(71) Applicant: CUREMETA THERAPEUTICS, LLC, Boston, MA (US)

(72) Inventors: William Michael Schopperle, Boston, MA (US); Edwin Saavedra Tan, Roxbury Crossing, MA (US); Yawen Ju, Winchester, MA (US); Mats Harald Holmqvist, Malden, MA (US); Youngbin Tak, Boston, MA (US); An Mary Holmqvist, Malden, MA (US)

(73) Assignee: CUREMETA THERAPEUTICS, LLC, Boston, MA (US)

( * ) Notice: Subject to any disclaimer, the term of this patent is extended or adjusted under 35 U.S.C. 154(b) by 246 days.

(21) Appl. No.: 15/457,050

(22) Filed: Mar. 13, 2017

(65) Prior Publication Data
US 2017/0328907 A1 Nov. 16, 2017

Related U.S. Application Data

(60) Provisional application No. 62/307,690, filed on Mar. 14, 2016.

(51) Int. Cl.
*C07K 16/00* (2006.01)
*G01N 33/577* (2006.01)
*A61K 51/10* (2006.01)
*C07K 16/28* (2006.01)
*G01N 33/58* (2006.01)

(52) U.S. Cl.
CPC ........... *G01N 33/577* (2013.01); *A61K 51/10* (2013.01); *C07K 16/28* (2013.01); *G01N 33/582* (2013.01); *C07K 16/00* (2013.01); *C12N 2506/02* (2013.01)

(58) Field of Classification Search
None
See application file for complete search history.

(56) References Cited

FOREIGN PATENT DOCUMENTS

WO WO2014170549 * 10/2014

* cited by examiner

*Primary Examiner* — Lei Yao
(74) *Attorney, Agent, or Firm* — Eckert Seamans Cherin & Mellott, LLC; Carol A. Marmo

(57) ABSTRACT

The invention relates to an antibody or an antigen-binding fragment thereof, including a heavy chain and a light chain, with heavy chain complementarity determining regions 1 to 3 having the amino acid sequences of SEQ ID NOS. 1 to 3, respectively, and light chain complementarity determining regions 1 to 3 having the amino acid sequences of SEQ ID NOS. 4 to 6, respectively. In addition, the invention relates to an anti-cancer therapeutic agent including the antibody or the antigen-binding fragment thereof.

8 Claims, No Drawings

Specification includes a Sequence Listing.

_US 10,509,038 B2_

SEQUENCE LISTING

```
<160> NUMBER OF SEQ ID NOS: 6

<210> SEQ ID NO 1
<211> LENGTH: 8
<212> TYPE: PRT
<213> ORGANISM: Mus musculus

<400> SEQUENCE: 1

Gly Phe Thr Phe Ser Asp Phe Tyr
1               5

<210> SEQ ID NO 2
<211> LENGTH: 10
<212> TYPE: PRT
<213> ORGANISM: Mus musculus

<400> SEQUENCE: 2

Ser Arg Asn Lys Ala Asn Asp Tyr Thr Thr
1               5                   10

<210> SEQ ID NO 3
<211> LENGTH: 11
<212> TYPE: PRT
<213> ORGANISM: Mus musculus
```

```
<400> SEQUENCE: 3

Ala Arg Asp Gly Trp Val Glu Ala Met Asp Tyr
1               5                   10

<210> SEQ ID NO 4
<211> LENGTH: 11
<212> TYPE: PRT
<213> ORGANISM: Mus musculus

<400> SEQUENCE: 4

Gln Ser Leu Val His Ser Asn Gly Asn Thr Tyr
1               5                   10

<210> SEQ ID NO 5
<211> LENGTH: 3
<212> TYPE: PRT
<213> ORGANISM: Mus musculus

<400> SEQUENCE: 5

Lys Val Ser
1

<210> SEQ ID NO 6
<211> LENGTH: 9
<212> TYPE: PRT
<213> ORGANISM: Mus musculus

<400> SEQUENCE: 6

Ser Gln Ser Thr His Val Pro Trp Thr
1               5
```

PODOCALYXIN AND TRA-RELATED ANTIBODY, METHODS OF PREPARATION AND USES AS AN ANTI-CANCER THERAPEUTIC AGENT

CROSS-REFERENCE TO RELATED APPLICATIONS

This application claims priority under 35 U.S.C. § 119(e) from U.S. provisional patent application No. 62/307,690, entitled "PODOCALYXIN AND TRA-RELATED ANTIBODY, METHODS FOR PREPARATION AND USES FOR TREATMENT OF AGGRESSIVE AND/OR METASTATIC CANCER", filed on Mar. 14, 2016, the contents of which are incorporated herein by reference in its entirety.

FIELD OF THE INVENTION

This invention relates to a pluripotent- and an embryonic stem cell-specific antibody. This invention further relates to an antibody which is reactive and has binding activity to the embryonic form of the Podocalyxin protein. This invention further relates to a cancer therapeutic agent, which includes the antibody or an antibody fragment thereof, as an active ingredient to regress, reduce or eliminate cancer cells.

BACKGROUND OF THE INVENTION

Normal human embryonic stem cells are pluripotent stem cells that differentiate into the two-hundred different types of cells that make up the human body. Embryonal carcinoma is a human cancerous pluripotent stem cell derived from human germ cell tumors and is known as the malignant equivalent of normal embryonic stem cells. Both normal embryonic stem cells and embryonal carcinoma express pluripotent-associated antigens on the surface of their plasma membrane. It is known that at least some pluripotent-associated antigens are lost during differentiation and are not expressed or lowly expressed in normal cells and tissues.

It is known that many human cancers have an embryonic stem cell gene signature and re-express pluripotent and embryonic antigens not present or lowly present in normal differentiated cells. The Cellular Reprogramming theory of the origin of cancer states that the cause of cancer is due to a normal cell reprogramming and undergoing dedifferentiation backwards towards a primitive embryonic-like cancer cell with stem cell properties. It is believed these primitive embryonic-like cancer stem cells are the origin of cancer and are the drivers of disease progression, and disease resistant which almost universally occurs with conventional therapies. Furthermore, it is thought that therapeutic targeting and eliminating of these primitive embryonic-like cancer stem cells will result in meaningful and lasting cancer treatments.

Podocalyxin is a cell surface glycoprotein that is highly expressed on human embryonic stem cells and pluripotent cancer stem cells. The podocalyxin protein expressed on embryonic and pluripotent cells has additional carbohydrate groups (TRA-1-60 and TRA-1-81 which are herein referred to as TRA) attached to the podocalyxin protein. The TRA carbohydrate groups are embryonic and pluripotent specific and are not present on somatic or differentiated cells. The pluripotent and embryonic version of podocalyxin is call TRA-Podocalyxin. It is known that the embryonic and pluripotent form TRA-Podocalyxin is re-expressed in many types of cancer Monoclonal antibodies can be produced that are specific and reactive to pluripotent antigens expressed on the surface of cancer cells and normal embryonic cells, but not on normal differentiated cells of the body. Furthermore, monoclonal antibodies can be produce that are reactive and have specific binding activity to TRA-Podocalyxin. These antibodies can be used as anti-cancer therapeutic agents for cancers which re-express embryonic and pluripotent antigens such as TRA-Podocalyxin during the onset and progression of the disease.

It is an object of the invention to develop a pluripotent- and an embryonic stem cell-specific antibody. In addition, it is an object of the invention to develop a TRA-Podocalyxin specific antibody. Further, it is an object to develop a therapeutic agent or composition that includes the antibody or a fragment thereof as an active ingredient. Furthermore, it is an object to introduce or administer the therapeutic agent or composition to a cancer patient to regress, reduce or eliminate cancer cells in the patient.

SUMMARY OF THE INVENTION

The monoclonal antibody in accordance with the invention includes six specific amino acid sequences that have three heavy chain complementarily determining regions and three light chain complementarity determining regions.

The monoclonal antibody can be specific and reactive to cell surface plasma membrane of human embryonic stem cells and malignant embryonal carcinoma pluripotent stem cells. Furthermore, the monoclonal antibody can be specific and reactive to TRA-Podocalyxin.

The monoclonal antibody can have specificity and reactivity to a plurality of human cancers selected from the group consisting of oral, ovarian, prostate, breast, pancreatic, colon, gastric and esophageal.

In one aspect, the invention provides a monoclonal antibody or an antigen-binding fragment thereof, comprising a heavy chain and a light chain, with heavy chain complementarity determining regions 1 to 3 having the amino acid sequences of SEQ ID NOS. 1 to 3, respectively, and light chain complementarity determining regions 1 to 3 having the amino acid sequences of SEQ ID NOS. 4 to 6, respectively.

The antibody or fragment thereof can be a recombinant antibody. The recombinant antibody is selected from the group consisting of a human chimeric antibody, a humanized antibody and a human antibody.

In certain embodiments, a fragment is selected from the group consisting of a Fab, a Fab', a F(ab')2, a scFv, a Diabody, a dsFv and a peptide comprising CDR.

In another aspect, the invention provides a monoclonal antibody or an antigen-binding fragment thereof, including a heavy chain and light chain, with heavy chain complementarity determining regions 1 to 3 having at least 80% amino acid sequence similarity to the amino acid sequences of SEQ ID NOS. 1 to 3, respectively, and the light chain complementarity determining regions 1 to 3 having the amino acid sequences of SEQ ID NOS. 4 to 6, respectively.

Furthermore, the light chain complementarity determining regions 1 to 3 can have at least 80% amino acid sequence similarity to the amino acid sequences of SEQ ID NOS. 4 to 6, respectively.

The antibody or fragment thereof can be a recombinant antibody. The recombinant antibody is selected from the group consisting of a human chimeric antibody, a humanized antibody and a human antibody.

In certain embodiments, a fragment is selected from the group consisting of a Fab, a Fab', a F(ab')2, a scFv, a Diabody, a dsFv and a peptide comprising CDR.

In still another aspect, the invention includes an anti-cancer therapeutic agent, including the monoclonal antibody or antigen-binding fragment above-described.

The agent can be in a composition form further including a component selected from the group consisting of a pharmaceutically acceptable linker, payload and combinations thereof. The agent can be in a composition form further including a drug to form an antibody-drug-conjugate. The agent can target, select and eliminate embryonic stem cells from differentiated cells derived from embryonic stem cells. The agent can target cancer cells selected from the group consisting of gastric, pancreatic, esophageal, colon, breast and prostate cancer cells.

The composition can be administered to a patient by intravenous delivery of the antibody in its naked human chimeric form to elicit anti-tumor antibody-dependent cellular cytotoxicity. Alternately, the composition can be administered to a patient by intravenous delivery, wherein the composition further includes a cytotoxic drug for delivery specifically to the cancer cell.

SEQUENCE LISTING

The amino acid sequences listed in the accompanying sequence listing are shown using standard letter abbreviations and the sequence listing is incorporated by reference herein.

DETAILED DESCRIPTION OF THE INVENTION

The invention relates to a pluripotent- and an embryonic stem cell-specific antibody. The antibody demonstrates and-tumor activity. The antibody is unreactive or poorly reactive to normal cells, and is highly specific and reactive to a plurality of cancer cells. The antibody can be used as an anti-cancer therapeutic agent through its antibody-dependent cellular cytotoxicity properties, complement-dependent cytotoxicity properties, and an antibody-drug conjugate. The antibody conjugated with toxin, for example, has a cytotoxic activity against cancer cells. The antibody is effective against a wide variety of cancers including, but not limited to, oral, ovarian gastric, pancreatic, esophageal, colon, breast and prostate cancers.

The antibody of the invention is monoclonal and referred to herein as Bstrongomab-9A or CM-918. The monoclonal antibody is produced using standard hybridoma technology. The DNA and amino acid sequence of the variable regions of the heavy and light chains of monoclonal antibody CM-918 are described herein. The amino acid sequences of the complementarity determining regions (CDR) were defined using VBASE2.

The monoclonal antibody CM-918 includes amino acid sequences of heavy chain complementarity determining regions (hcCDRs) 1 to 3, as follows:

```
hcCDR #1
                              (SEQ ID NO. 1)
GFTFSDFY hcCDR #2
                              (SEQ ID NO. 2)
SRNKANDYTT hcCDR #33
                              (SEQ ID NO. 3)
ARDGWVEAMDY
```

The monoclonal antibody CM-918 includes amino acid sequences of light chain complementarity determining regions (lcCDRS) 1 to 3, as follows:

```
lcCDR #1
                              (SEQ ID NO. 4)
QSLVHSNGNTY lcCDR #2
                              (SEQ ID NO. 5)
KVS lcCDR #33
                              (SEQ ID NO. 6)
SQSTHVPWT
```

The monoclonal antibody CM-918 can be a recombinant antibody including non-human and human antibody. In alternate embodiments, the recombinant antibody can be non-human animal-derived antibody (e.g., a mouse or rat), human-derived antibody, human chimeric antibody, or humanized antibody. The antibody is preferably an anti-human antibody, which specifically binds to human cells e.g., pluripotent and embryonic stem cells. More particularly, the antibody is a mammal-derived monoclonal antibody, which encompasses those produced by hybridomas. In certain embodiments, the antibody is mouse-derived using conventional hybridoma technology. The antibody may be modified with various molecules, such as, but not limited to polyethylene glycol (PEG). The antibody' may also be modified with a chemotherapy agent, a radioactive chemical, or the like, having cytotoxic activity.

In certain embodiments, the monoclonal antibody CM-918 has reactivity and selective binding to an epitope can the cell adhesion protein Podocalyxin (also known as Podocalyxin-like protein 1). Podocalyxin is an integral membrane protein that, in humans, is encoded by the PODXL gene. Podocalyxin is a heavily glycosylated type-1 transmembrane protein expressed in some normal cells. Podocalyxin is highly expressed in a variety of cancers and is a tumor marker, in which its level of expression correlates with tumor aggressiveness in various cancers. Podocalyxin has a molecular weight in normal cells of about 160-164 kDa. Podocalyxin is also heavily expressed in normal embryonic stem cells and malignant pluripotent embryonal carcinoma stem cells. Podocalyxin is a cell surface marker of normal embryonic stem cells. Podocalyxin is expressed in all embryonic and pluripotent stem cells in an embryonic or pluripotent-specific variant form, which has additional post-translational modifications that are not present in non-pluripotent and embryonic stems cells. One known embryonic stem cell-specific post translational modification of podocalyxin is an additional glycosylation of the podocalyxin protein backbone known as TRA-1-60 and TRA-1-81 (herein referred to as the TRA epitope). Without intending to be bound by any particular theory, it is believed that the TRA epitope is an extended tetrasaccharide mucin type O-glycan structure that is pluripotent- and embryonic-specific. When embryonic stem cells and pluripotent cancer cells differentiate into somatic cells, the TRA epitope is lost from podocalyxin. TRA is not expressed on normal somatic and differentiated cells. The apparent molecular weight of the embryonic variant of podocalyxin with the TRA epitopes (herein referred to as TRA-Podocalyxin) is about 200-240 kDa. It is known that TRA-Podocalyxin is expressed in many types of cancer including oral, colon, pancreatic, gastric, breast, prostrate, brain, ovarian, and lung cancers. In certain embodiments of the invention, the monoclonal antibody CM-918 is reactive and has selective binding to the TRA epitope present on the embryonic and pluripotent variant of podocalyxin, TRA-Podocalyxin.

In other embodiments, the monoclonal antibody CM-918 has selective binding and reactivity to an unknown epitope on TRA-Podocalyxin. In still other embodiments, the monoclonal antibody CM-918 has selective binding and reactivity to an unknown epitope which is expressed on the cell plasma membrane of embryonic stem cells and pluripotent embryonal carcinoma cancer cells. It is understood and contemplated in accordance with the invention that there are amino acid sequence variants of CM-918 antibody, in which one or two or three amino acids in one or more of the heavy chain CDRs sequences (SEQ ID NOS. 1 to 3) are replaced with another amino acid. Preferably, these CM-918 variants have reactivity and selective binding to TRA-Podocalyxin, or reactivity and selective binding to the cell surface plasma membrane of embryonic stem cells.

Amino acid sequence variants of CM-918 antibody in which one or two or three amino acids in one or more of the light chain CDRs sequences (SEQ ID NOS. 4 to 6) are replaced with another amino acid, are also understood and contemplated in accordance with the invention. Preferably, these CM-918 variants have reactivity and selective binding to TRA-Podocalyxin or reactivity and selective binding to the cell surface plasma membrane of embryonic stem cells.

In certain aspects, the invention provides an antibody including a heavy chain CDR1 having the amino acid sequence as set forth in SEQ. ID NO. 1, as well as CDR2 and CDR3 having the amino acid sequences as set forth in SEQ ID NO. 2 and SEQ ID NO. 3, respectively. Further, the antibody includes light chain CDR1 having the amino acid sequence as set forth in SEQ ID NO. 4, as well as CDR2 and CDR3 having amino acid sequences as set forth in SEQ ID NO. 5 and SEQ ID NO. 6, respectively. Furthermore, in certain aspects, the invention incorporates an antibody derived from, and functionally equivalent to, the antibody described herein by the substitution, deletion, addition and/or insertion of one or more amino acids. In certain aspects, the invention includes a monoclonal antibody or an antigen-binding fragment thereof, comprising a heavy chain and light chain, with heavy chain complementarity determining regions 1 to 3 having at least 80% amino acid sequence similarity to the amino acid sequences of SEQ ID NOS. 1 to 3, respectively, and the light chain complementarity determining regions 1 to 3 having the amino acid sequences of SEQ ID NOS. 4 to 6, respectively. In certain other aspects, the invention includes a monoclonal antibody or an antigen-binding fragment thereof, comprising a heavy chain and light chain, with heavy chain complementarity determining regions 1 to 3 having the amino acid sequences of SEQ ID NOS. 1 to 3, respectively, and the light chain complementarity determining regions 1 to 3 having at least 80% amino acid sequence similarity to the amino acid sequences of SEQ ID NOS. 4 to 6, respectively. In yet certain other aspects, the invention includes a monoclonal antibody or an antigen-binding fragment thereof, comprising a heavy chain and light chain, with heavy chain complementarity determining regions 1 to 3 having at least 80% amino acid sequence similarity to the amino acid sequences of SEQ ID NOS. 1 to 3, respectively, and the light chain complementarity determining regions 1 to 3 having at least 80% amino acid sequence similarity to the amino acid sequences of SEQ ID NOS. 4 to 6, respectively.

The antibody of the invention is not limited to whole antibody molecules and may be a low-molecular antibody or a modified form thereof, as long as the antibody binds to the cell surface. The low molecular antibody encompasses an antibody fragment deficient in a portion of the whole antibody. Such partial deficiency of the antibody molecule is acceptable as long as the resultant antibody fragment is capable of binding to the cell surface. It is preferred that the antibody fragment contains the heavy chain (hc) CDRs as set forth in SEQ ID NOS. 1, 2 and 3, and the light chain (lc) CDRs as set forth in SEQ ID NOS. 4, 5 and 6. Specific examples of the low molecular antibody and antibody fragment can include Fab, Fab', F(ab')2, scFv (single chain Fv), dsFv Diabody, sc(Fv)2 or a peptide including CDR.

The Diabody refers to a bivalent antibody fragment constructed by gene fusion. The Diabody is a dimer comprising two polypeptide chains. The say is obtained by linking heavy and light chain regions of the antibody. In the scFv, the heavy and light chain regions are linked via a linker, such as, a peptide linker. The peptide linker that links the. variable regions is not particularly limited. For example, an arbitrary single chain peptide of approximately 3 to 25 residues can be used as the linker. The scFv-Fc is a low-molecular antibody comprising an Fc region fused to scFv. The origin of the scFv used in the scFv-Fc is not particularly limited, and for example, scFv derived from IgM can be used. Moreover, the origin of the Fc is not particularly limited, and, for example, Fc derived from human IgG (human IgG1, etc.) can be used. The sc(Fv)2 is a low-molecular antibody having a single chain comprising heavy chain regions and light chain regions linked via linkers or the like. The sc(Fv)2 can be prepared, for example, by linking says via a linker.

Fragments of the antibody can be obtained by using various technologies known in the art, such as, but not limited to, enzymatically treating the antibody to form fragments thereof.

For the treatment of cell-proliferative disease such as cancer, it is preferred that the antibody maintain its effector activity. Specifically, an antibody according to the present invention may have both a binding affinity for cell surfaces and effector functions. The effector functions of the antibody encompass an antibody-dependent cell-mediated cytotoxic (ADCC) activity and a complement-dependent cytotoxic (CDC) activity. The therapeutic antibody according to the present invention may particularly possess ADCC activity as effector functions. The antibody of the present invention used for therapeutic purposes may be an antibody having a cytotoxic activity. Examples of the cytotoxic activity according to the present invention can include ADCC and CDC activities. In the present invention, ADCC activity means the activity of damaging target cells through the binding of Fcγ receptor-bearing cells (immunocytes, etc.) via the Fcγ receptors to the Fc domains of antibodies specifically attached to the cell surface antigens of the target cells. The CDC activity means a cytotoxic activity mediated by the complement system.

The antibody may be conjugated with a cytotoxic substance. Non-limiting examples of suitable cytotoxic substances include a chemotherapeutic agent, a toxic peptide, a radioactive chemical, or other payload, such as a drug. Such a modified antibody (hereinafter, referred to as an antibody conjugate) can be obtained by chemically modifying the obtained antibody. In certain embodiments, the modified antibody includes a pharmaceutically acceptable linker, a payload or combinations thereof. Wherein the payload is a drug, an antibody-drug-conjugate is formed. Various methods for antibody modification are known in the art, and these methods are suitable for use in accordance with the present invention.

The present invention provides a pharmaceutical composition including the antibody, which binds to surfaces of cells, e.g., pluripotent and embryonic stem cells, as an active ingredient. The pharmaceutical composition includes a therapeutically effective amount of the antibody. The term "therapeutically effective amount" indicates an amount of the antibody which enables the antibody to exert a desired therapeutic effect or prophylactic effect. In an embodiment, the pharmaceutical composition is a cell growth inhibitor, particularly, an anti-cancer therapeutic agent. The cell growth inhibitor and the anti-cancer agent of the present invention are administered to a subject having cancer or possibly having cancer, and may be effective to target, select and eliminate embryonic stem cells from differentiated cells derived from embryonic stem cells.

The pharmaceutical composition of the present invention may comprise a cytotoxic substance-conjugated antibody as an active ingredient. When the disease targeted by the pharmaceutical composition of the present invention is cancer, the targeted cancer is not particularly limited and may be, in particular, oral, ovarian, gastric cancer, pancreatic cancer, esophageal cancer, colon cancer, breast cancer or prostate cancer.

The pharmaceutical composition of the present invention can be administered either orally or parenterally to a patient. Parenteral administration may be preferable. Specific examples of such an administration method include injection, transnasal, pulmonary, and transdermal administrations. Examples of the injection administration include intravenous, intramuscular, intraperitoneal, and subcutaneous injections, through which the pharmaceutical composition of the present invention can be administered systemically or locally. Moreover, the administration method can be selected appropriately according to the age or symptoms of the patient. The dose of the pharmaceutical composition of the present invention can be selected from among a dose range of, for example, 0.0001 mg to 1000 mg per kg body weight per dosing. Alternatively, the dose can be selected from among a range of, for example, 0.001 to 100000 mg per body. However, the pharmaceutical composition of the present invention is not limited to these doses, The pharmaceutical composition of the present invention can be formulated according to standard, conventional methods that are known in the art, and may conventionally contain pharmaceutically acceptable carriers or additives. Examples thereof include, but not limited thereto, surfactants, excipients, coloring agents, flavoring agents, preservatives, stabilizers, buffers, suspending agents, tonicity agents, binders, disintegrants lubricants, flow promoters, and corrigents. Other carriers routinely used can be incorporated appropriately. Upon contact with cancer cells, the antibody of the present invention can damage the cancer cells or inhibit their growth. The cells to which the antibody binds are not particularly limited. In the present invention, cells are preferably cancer cells.

It will be appreciated by those skilled in the art that changes can be made to the embodiments described above without departing from the broad inventive concept thereof. It is understood, therefore, that this invention is not limited to the particular embodiments disclosed and the following examples conducted, but it is intended to cover modifications that are within the spirit and scope of the invention.

EXAMPLES

Example 1

Preparation of the Monoclonal Antibody CM-918

The monoclonal antibody of the invention, referred to herein as Bstrongomab or CM-918, was produced using standard mouse hybridoma technology. Mice were injected intraperitoneally with freshly harvested NCCIT cells suspended in sterile PBS. Each mouse received 10e6 cells per injection. After four injections spaced every 2 two weeks, the serum of immunized mice were tested on an ELISA and Western Blot assay to identify mice with positive titers. The mouse with the highest titer then received a prelusion boost immunization 2-7 days before harvesting B cells from the spleen and fusion to NS0 or P3X63Ag8.653 mouse myeloma Hybridomas were plated into 96 well plates (960 wells per fusion) and propagated for 14 days with hybridoma fusion media comprised of 20% fetal bovine serum, 20% NCTC-109 (Gibco), 1% v/v penicillin-streptomycin, 2 mM L-Glutamine, 0.4% v/v hybridoma fusion and cloning supplement (Sigma-Aldrich), 1× non-essential amino acids (Gibco), 1×HAT-Supplement (Gibco), 20 mM HEPES, and RPMI 1640 medium (mod.) 1× with L-Glutamine. Hybridoma supernatants were collected and screened by western blot against NCCIT lysate to identify hybridomas generating IgG antibodies binding to TRA. Positive clones were scaled and subjected to at least two rounds of limited dilution subcloning in 96 well plates to isolate monoclonal hybridomas. Subcloning plates were screened by ELISA and positive, monoclonal hybridomas were scaled in hybridoma media comprised of 10% fetal bovine serum, 10% NCTC-109 (Gibco), 1% v/v penicillin-streptomycin, 2 mM L-Glutamine, 0.4% hybridoma fusion and cloning supplement (Sigma-Aldrich), 1× non-essential amino acids (Gibco), 1×HT-Supplement (Gibco), 20 mM HEPES, and RPMI 1640 medium (mod.) 1× with L-Glutamine.

After confirming the hybridoma activity in western blot assays, the monoclonal hybridomas were cryofrozen in hybridoma media supplemented with 10% DMSO. CM-918 antibodies were purified from the supernatants of monoclonal hybridomas cultured to exhaustion in hybridoma media containing 10% ultra-low IgG PBS. The supernatants were centrifuged and then passed through a 45 um filter to remove cells and cellular debris. The IgG antibodies were purified by affinity chromatography using the HiTrap Protein G HP columns from GE LifeSciences. Purified mAbs were desalted using Zeba Spin Desalting Columns (ThermoScientific). The heavy and light chain variable regions were DNA sequenced and the amino acid sequences of the CDR regions of the antibody was defined by using VBASE2, an integrative database of germ-line variable genes from the immunoglobulin loci of human and mouse.

Example 2

Western Blot Analysis of Pluripotent Cells with CM-918 Antibody

A western blot of membrane proteins samples from pluripotent embryonal carcinoma cancer cells NCCIT (ATCC # CRL2073) and human embryonic stem cells (ESI-017) using CM-918 antibody showed a single diffuse band at 200-240 kDa molecular weight in both protein membrane preps, but no reactivity was detected in non-pluripotent cell lines PC3 (ATCC CRL1435) or A172 (ATCC CRL1620) that do not express TRA-Podocalyxin. Identical blot results were obtained using a commercially available IgM antibody, anti-TRA-1-60 (abcam 16288) on identical western blots. The results confirm that CM-918 antibody and the anti-TRA-1-60 antibody bind to a similar epitope. SDS-PAGE and Western blotting were performed by standard methodology. Cell membrane preps in 1% Chaps detergent (Sigma)

in phosphate buffer were run on 8% gels and transferred to nitrocellulose. Blots were incubated with CM-918 or Anti-TRA-1-60 antibodies at 1:1000 (1 ug/ml concentration) followed with incubation of secondary anti-IGG-HRP or anti-IGM-HRP antibodies at 1-5000 (0.2 ug/ml) (Millipore) and bands were visualized by ECL detection (Amersham Biosciences).

Example 3

CM-918 Antibody Plasma Membrane Staining of Embryonic Stem Cells and Pluripotent Embryonal Carcinoma Cells Embryonic stem cells (ESL-017) and pluripotent NCCIT embryonal carcinoma cells were stained with CM-918 antibody conjugated with Alexa 647 (Sigma) (0.5 ug/ml) and with anti-TRA-1-60 antibody (0.5 ug/ml) and and-IgM-Alexa F488 antibody (Millipore) (0.5 ug/ml). Fluorescence microscopy images with red channel showed CM-918 antibody binds strongly to the plasma membrane of embryonic stem cells and pluripotent embryonal carcinoma cells, but not to control cell lines PC3 (ATCC 4 CRL1435) or A172 (ATCC # CRL1620) that do not express TRA-Podocalyxin. Superimposed fluorescence images from red and green channels showed identical staining overlap of CM-918 and anti-TRA-1-60 antibodies showing that both antibodies binding to same epitopes on the surface of the stem cells.

Example 4

Immunohistochemical (IHC) Staining of CM-918 Antibody on Normal Human Tissues and Human Cancers Immunohistochemical staining of normal tissues and cancers with the CM-918 was performed as described below. A grading system of 0 to 3 was used: 0 for no observed staining 1 for focal staining 5%); 2 for moderate staining (<50%); and 3 for strong staining (>50%). Stained tissue slides were scored by a Pathologists. Staining scores of 2 or 3 were observed in the following cancer tissues: Pancreatic cancer 22 of 38 samples; Prostatic cancer 19 of 41 samples; breast cancer 45 of 145 samples; Ovarian cancer 18 of 30 samples; gastric cancer 8 of 8 samples; colon cancer 15 of 30 samples; and lung cancer 32 of 66 samples. Expression in normal human tissues was very limited ranging from zero expression in almost all normal tissues including bone marrow and minor focal expression in some cases of pancreas, esophagus and colon. Kidney has positive scoring in all samples with about 1% of CM-918 staining in tubules. The only normal tissue which had a scoring of 2 was the parathyroid which had 2 of 9 samples with a 2-staining score. The results show that CM-918 has membrane staining in many different cancers and has very limited straining in normal tissues.

All tissues were fixed in 10% buffered formalin for 24 hours, sectioned at 5 microns and placed on positively charged slides. Before staining, slides were dried at 60 degree overnight. After deparaffinized in Xylene (Fisher Scientific, Cat# X3P-1GAL), sections were rehydrated through 100% Ethanol (Eki-Chem, Cat# 4085-IGL), 95% Ethanol and 70% Ethanol (Eki-Chem, Cat# 4089-I(L). Sections were then immersed into 1× Diva Decloaker (Biocare Medical, Cat# DV2004LX), and cooked with Decloaking chamber (Biocare Medical, Model: NxGen). Afterwards, sections were blocked by BLOXALL (Vector labs, Cat# SP-6000) and PowerVision Universal IHC Blocking/Dilution (Leica, Cat# BD09-15). Primary antibody was applied to each slide at 2 ug/ml in PBS, leaving at room temperature for 1 hour. After washing by PBS, PowerVision Post Blocking (Leica, Cat# DPVO+15Post) was applied for 20 min at room temperature Then slides were incubated with PowerVision Poly-HRP anti-Mouse/Rabbit IgG (Leica Cat# DPVO-15HRP) for 30 min at room temperature, followed by DAB (Vector labs, Cat# SK4105) color reaction. Slides were countermined with hematoxylin (Vector labs, Cat# 3404). Between incubations of different reagents or antibodies, slides were washed by PBS. Embryonal carcinoma sections were included in staining in order to assure technical accuracy of target protein expression in tissues. Negative control experiments were conducted in the presence of isotype control antibodies (Biolegend, Cat# 401401), in parallel of all assays.

Example 5

Cell Viability Dose Response Curves of CM-918-Antibody-Drug-Conjugate

A CM-919-vc-MMAE antibody drug conjugate was made: A solution of CM-918 in PBS was treated with TCEP at 37 C to reduce the inter-chain disulfide bonds. A solution of MC-vc-PAB-MMAE (maleimidedocaproyl-valine-citruline-p-aminobenzyloxycarbonyl-monomethyl auristatine E) was added to the reaction mixture to link the maleimide moiety of MC-vc-PAB-MMAE to CM-918. The resulting antibody drug conjugate (ADC) was desalted on a Sephadex G50 column to remove residual unreacted toxins and to buffer exchange into PBS (pH 7.2). The drug antibody ratio (DAR) was determined from the ratio of UV absorbance at 248 and 260 nm. HIC (Hydrophobic Interaction Chromatography) and SEC (Size Exclusion Chromatography) analysis were performed to determine DAR species distribution.

A cell viability assay with pluripotent NCCIT cells, embryonic stem cells (ESL-017) and control PCS cells which do not express TRA-podocalyxin was preformed: Seed target cells into 96-well plates at density of $3 \times 10^3$ to $1 \times 10^4$ cells per well (90 ul) and incubate the cells in 5% CO2 incubator for 24 hours. Treat the cells with antibody (10 ul per well) as following: start concentration at 100 nM and half log dilution down, 6 replicates per concentration, and the last wells without antibody treatment is used as negative control. Incubate the cells in 5% CO2 incubator for 24 hours to 7 days. Equilibrate the CellTiter-Glo® Luminescent Cell. Viability Assay Reagent (Promega, catalog number 7572) to room temperature before use. Apply 100 ul of CellTiter-Glo® Reagent into each well and mix contents for 2 minutes on an orbital shaker to induce cell lysis. Allow the plate to incubate at room temperature for 10 minutes to stabilize the luminescent signal. Record luminescence on a Microplate Reader (Filtermax F5, Molecular Devices, Sunnyvale, Calif.).

The results of the cell viability assay showed that the IC50 killing of cells with the CM-918-vc-MMAE antibody drug conjugate was 2.7 nM for the NCCIT cells, 5.6 nM for the embryonic stem cells and no effect was observed on the control PC3 cells up to a concentration of 100 nM of the CM-918-vc MMAE. An iso-type control antibody conjugated identically with MMAE has no effect on all three cell lines at concentrations up to 100 uM. The results show that CM-918 antibody drug conjugate is very effective at killing pluripotent embryonal carcinoma cancer cells and human embryonic stem cells, but not cells which do not express the TRA-podocalyxin.

Example 6

Pluripotent NCCIT Cancer Cell/Mouse Xenograft Model Treated with CM-919 Antibody Drug Conjugated Fifteen nude mouse were injected subcutaneously with 2×106 NCCIT pluripotent cancer stem cells and tumors were allowed to develop into 200 mm³ size at which time the mice were divided into 3 groups of 5: 5 mice were treated with 4 injections of saline; 5 mice were treated with CM-vc-MMAE at 3 mg/kg, Q4Dx4; the final five treated with an isotype antibody control-vc-MMAE at 3 mg/kg, Q4Dx4. The results show that at the end of 35 days both saline injected and isotype control injected mice had tumors with an average size of 1000 mm³. In the CM-918 antibody drug conjugated treated mice, 4 of the 5 mice had no detectable tumors and 1 mouse had a tumor of approximately 25 mm³. An isotype control antibody conjugated with MMAE as with CM-918 showed similar results as the saline treated mice with an average tumor size of 1000 mm³. The results show that CM-919-vc-MMAE antibody drug conjugate is effective and potent at treating pluripotent cancer stem cell tumors in mice.

Example 7

Antibody Dependent Cellular Cytotoxicity Assay (ADCC) with CM-918 Antibody

ADCC assay using CM-918 antibody with pluripotent cancer NCCIT cells showed between 12-15% cytotoxicity and CM-918 ADCC activity with control cells not expressing TRA-Podocalyxin had 2% cytotoxicity. A control IgG antibody had 2% cytotoxicity with NCCIT cells. The results show that CM-918 antibody has ADCC activity with pluripotent cancer cells that express TRA-Podocalyxin.

Human PBMCs were purified from blood of healthy donors by using a Ficoll gradient. Target cells were seeded into 96-well plates at 1×104 /well and incubated with freshly isolated PBMCs at E:T=25:1 or 50:1 for 4 h at 37° C. The concentration of test antibody and IgG-Fc control antibody was fixed at 190 nm. After co-incubation, cell cytotoxicity was measured with LDH assay. Percent target cell cytotoxicity was calculated by background subtracting absorbance values by Effector and Target cells (no antibody) control, and scaling Target Cell only (spontaneous lysis) as 0% and lysed Target Cell only (maximal lysis) as 100%.

Example #8

Complement Dependent Cytotoxicity Assay (CDC) with CM-918 Antibody

A CDC assay was preformed and showed that NCCIT pluripotent cancer stem cells had 18% Cytotoxicity with 100 nM CM-918 antibody and 10% cytotoxicity with 10 nM. CM-918 antibody. The results of NCCIT cell cytotoxicity in a CDC assay using 100 nM control antibody had <1% cytotoxicity. These results show that CM-918 antibody can elicit CDC activity on pluripotent cancer stem cells that express TRA-podocalyxin on the plasma membrane cell surface.

Human complement was incubated with $10^4$ target cells at a 1:4 volume ratio in a 96-well format. Test antibody was loaded at a 10-point half-log dilution series starting at 190 nM. The IgG-Fc control antibody was only added 190 nM. Antibodies were co-incubated with target cells and complement for 4 h at 37° C. After co-incubation, cell cytotoxicity was measured with LDH assay (Roche). Percent target cell cytotoxicity was calculated by background subtracting absorbance values by Complement and Target cells (no antibody) control, and scaling Target Cell only (spontaneous lysis) as 0% and lysed Target Cell only (maximal lysis) as 100%.

What is claimed is:

1. A monoclonal antibody consisting of a heavy chain having the amino acid sequences of SEQ ID NOS. 1 to 3, and a light chain having the amino acid sequences of SEQ ID NOS. 4 to 6.

2. The monoclonal antibody of claim 1, wherein said antibody, is a recombinant antibody.

3. The monoclonal antibody of claim 2, wherein the recombinant antibody is a mouse-human chimeric antibody.

4. An anti-cancer therapeutic agent, comprising the monoclonal antibody of claim 1.

5. The anti-cancer therapeutic agent of claim 4, wherein said agent is in a composition form further comprising a component selected from the group consisting of a pharmaceutically acceptable linker, payload and combinations thereof.

6. The anti-cancer therapeutic agent of claim 4, wherein said agent is in a composition form further comprising a drug to form an antibody-drug-conjugate.

7. The anti-cancer therapeutic agent of claim 4, wherein said agent targets, selects and eliminates embryonic stem cells from differentiated cells derived from embryonic stem cells.

8. The anti-cancer therapeutic agent of claim 4, wherein said agent targets cancer cells selected from the group consisting of gastric, pancreatic, esophageal, colon, breast and prostate cancer cells.

* * * * *